United States Patent
Harsanyi et al.

[11] Patent Number: 6,140,336
[45] Date of Patent: Oct. 31, 2000

[54] SPIRO[2H-1-BENZOPYRAN-2,4'-PIPERIDINE]-4(3H)-ONE DERIVATIVES, ACID ADDITION SALTS THEREOF AND PHARMACEUTICAL COMPOSITIONS CONTAINING THEM

[75] Inventors: Kalman Harsanyi; Istvan Szabadkai; Istvan Borza; Egon Karpati; Bela Kiss; Margit Pellionisz; Sandor Farkas; Csilla Horvath; Katalin Csomor; Erzsebet Lapis; Istvan Laszlowsky; Sandor Szabo; Agnes Kis-Varga, all of Budapest; Judit Laszy, Nagykovacsi; Aniko Gere, Budapest, all of Hungary

[73] Assignee: Richter Gedeon Vegyeszeti Gyar Rt., Budapest, Hungary

[21] Appl. No.: 08/973,612

[22] PCT Filed: Apr. 3, 1997

[86] PCT No.: PCT/HU97/00012

§ 371 Date: Feb. 12, 1998

§ 102(e) Date: Feb. 12, 1998

[87] PCT Pub. No.: WO97/37630

PCT Pub. Date: Oct. 16, 1997

[30] Foreign Application Priority Data

Apr. 10, 1996 [HU] Hungary .................................. 9600928

[51] Int. Cl.⁷ .......................... C07D 487/10; A61K 31/44
[52] U.S. Cl. .............................. 514/278; 546/17
[58] Field of Search ................................ 546/17; 514/278

[56] References Cited

FOREIGN PATENT DOCUMENTS 0 431 943 A2   6/1991   European Pat. Off. .
27 45 306      4/1979   Germany .

OTHER PUBLICATIONS

Chem. Pharm. Bull., 29(12), pp. 3494 to 3498 (1981).
J. Med. Chem., 1992, 35, pp. 3973 to 3976.
Chem. Abstracts, vol. 95, No. 9, Aug. 31, 1981, 95:80736u; XP002048516.
H. J. Kabbe, Synthesis, Dec. 1978, pp. 886–887.
J. Med. Exp., 10, 93 to 102 (1964); M. Fekete and J. Borsy. Orvostudomany 33, 347 to 361 (1982).
Helv. Chim. Acta., 41, 1188 (1958).
J. Amer. Che. Soc., 68, 2108 (1946).
Synth. Comm. 20, 3537 (1990).

*Primary Examiner*—Alan L. Rotman
*Attorney, Agent, or Firm*—Herbert Dubno; Jonathan Myers

[57] ABSTRACT

The invention relates to novel spiro[2H-1-benzopyran-2,4'-piperidine]-4(3H)-one derivatives of formula (I),

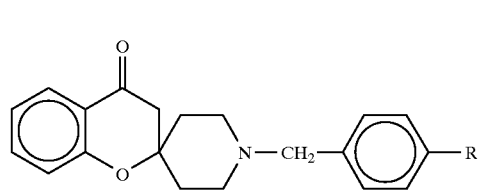

(I)

wherein R stands for halogen, nitro group or a straight or branched chain $C_{1-6}$ alkyl group, and their acid addition salts, as well as their quaternary salts of formula (Ia)

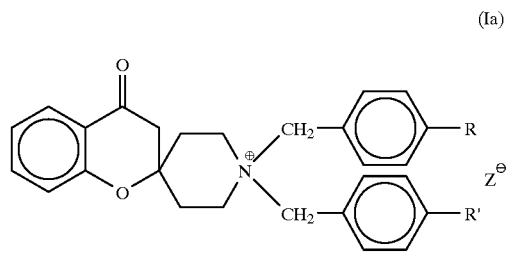

(Ia)

wherein R and R' are the same or different and are identical to the meaning of said (above) R or can mean also hydrogen; and Z represents one equivalent of an anion. The compounds of formulas (I) and (Ia) exert an improving effect on dementias of various pathological origin and accompanying symptoms thereof. Furthermore, the invention relates to a process for the preparation of compounds of formulas (I) and (Ia); to pharmaceutical compositions containing as active gents the above compounds of formulas (I) and (Ia); and to a method of treatment.

6 Claims, No Drawings

SPIRO[2H-1-BENZOPYRAN-2,4'-PIPERIDINE]-4(3H)-ONE DERIVATIVES, ACID ADDITION SALTS THEREOF AND PHARMACEUTICAL COMPOSITIONS CONTAINING THEM

CROSS-REFERENCE

This application is a 371 of PCT/HU97/00012 filed Apr. 3, 1997.

SPECIFICATION

The invention relates to novel spiro[2H-1-benzopyran-2,4'-piperidine]4(3H)-one derivatives of formula (I),

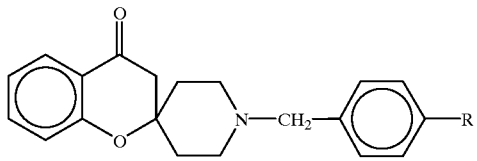

wherein

R stands for halogen, nitro group or a straight or branched chain $C_{1-6}$ alkyl group, and their acid addition salts, as well as their quaternary salts of formula (Ia),

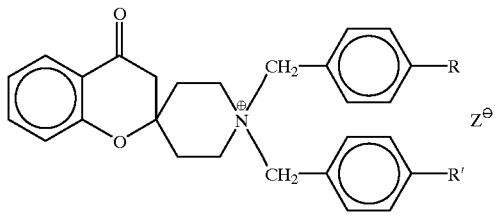

wherein

R and R' are the same or different and are identical to the meaning of said (above) R or can mean also hydrogen; and Z⁻ represents one equivalent of an anion.

The above compounds and salts exert a favorably influencing effect on dementias of various pathological origin or associated (accompanying) symptoms, respectively, thereof.

The invention also relates to pharmaceutical compositions containing and to methods of treatment employing as active ingredients novel or, wherein R means hydrogen, known spiro[2H-1-benzopyran-2,4'-piperidine]-4(3H)-one derivatives of formula (I) and/or pharmaceutically acceptable salts, and/or quaternary salts thereof of formula (Ia). These compositions favorably influence the dementias of various pathological origin or accompanying symptoms respectively, thereof.

Furthermore, the invention relates to the process of preparation of compounds of the formulas (I) and (Ia).

The invention relates also to a method of treatment, which comprises administering to a mammal, including man to be treated one or more effective dose(s) of a compound of formula (I) and/or pharmaceutically acceptable salts, and/or quaternary salts thereof of formula (Ia) for alleviating dementias of various pathological origin or the accompanying (associated) symptoms thereof.

Disturbances of various degree and progression of mental and cognitive functions (such as learning, memory, faculty of judgement and abstraction) are common characteristics of the dementias of various pathological origin, e.g.: Alzheimer's disease, multiinfarct dementias, states following stroke, dementias associated with Parkinson's disease or Huntington's chorea; or dementias occurring as sequels of hypoxia or poisonings. Since the life quality of both the patient and his surroundings are decisively determined by the integrity of psychic, mental and cognitive functions (learning, memory), one of the most important targets of the therapy of dementias of various aetiology is to prevent the impairment of the cognitive functions and to reverse the disturbances established and their sequels.

It has surprisingly been found that the spiro[2H-1-benzopyran-2,4'-piperidine]-4(3H)-one derivatives of formulas (I) and (Ia) possess a significant antiamnesic effect.

1'-Benzylspiro[2H-1-benzopyran-2,4'-piperidine]-4(3H)-one of formula (I) where R is hydrogen as well as some of its derivatives were described in Chem. Pharm. Bull. 29, 3494–3497 (1981). These compounds were investigated as inhibitors of the release of histamine from mast cells in comparison to disodium chromoglycate [chemically 1,3-bis(2-carboxy-4-oxochromen-5-yloxy)propan-2-ol disodium salt]. 1'-Benzylspiro[2H-1-benzopyran-2,4'-piperidine]-4(3H)-one was prepared by boiling 1-benzyl-4-piperidone with 2-hydroxy-acetophenone under reflux in a methanolic medium in the presence of pyrrolidine. A reaction of similar type had previously been carried out between certain ketones and 2-hydroxyacetophenone in toluene by the addition of pyrrolidine [Synthesis 886 (1978)]. An advantageous feature of the method resides in that the water formed during the cyclocondensation may azeotropically be distilled off.

According to the Chem. Pharm. Bull. publication cited above, the melting point of 1'-benzylspiro[2H-1-benzopyran-2,4'-piperidine]-4(3H)-one of formula (I) where R is hydrogen is at 91–93° C. However, it has been shown in our reproduced experiments directed to the preparation of this compound, that its melting point was about 10° C. higher (103–104° C.) in each case and independently thereof whether it was prepared by process a) or b). This observation may only be explained by either a high degree of contamination or by a chemical structure different from the published one of the compound described in the literature.

A much wide scope of sprio[2H-1-benzopyran-2,4'-piperidine]4(3H)-one derivatives are concerned by the European patent application No. 0,431,943 A2 relating to antiarrhythmic agents of III. class. A very broad variety of target compounds according to this patent document are defined on the basis of generic formulas; teachings by name are given only to a much more restricted scope of these compounds. Their compounds illustrated, which are structurally related to the target compounds of our invention, are characteristically distinct from those of our invention from the view point of substituents. In general, they are characterized by a substituent (e.g. methanesulfonylamino, methoxy, methylthio, dimethylamino or acetamido group) in position 6 of the ring system. They are further characterized in that the aromatic substituent (if present) is connected to the nitrogen through an alkyl chain containing at least two atoms. The most closely related compound disclosed is 1'-[2-(2-(p-nitrophenyl)ethyl]-spiro[2H-1-benzopyran-2,4'-piperidine]-4(3H)-one hydrochloride hemihydrate (Example 68). No specific pharmacological results are disclosed in this patent application. The really effective substances of the bulky content of this patent document are emphasized in J. Med. Chem. 35. 3973 (1992); these are common 6-methanesulfonylamino derivatives and bear a 2-aryl-ethyl or a 2-heteroarylethyl substituent on heterocyclic nitrogen in every case. Only one single derivative is disclosed, which does not contain any substituent in position 6, which is, however, an 1'-2-(2-pyridyl)ethyl] derivative.

It can be stated from those described above that, from compounds of formula (I), 1'-benzylspiro[2H-1-benzopyran-2,4'-piperidine]-4(3H)-one where R is hydrogen is the only one known (if the melting point deviation mentioned above is not considered), but its quaternary derivative of formula (Ia) is also novel.

Based on the revealed therapeutical effect of known, structurally related compounds it could not be expected that compounds of formulas (I) and (Ia) could have a favorable influence on dementias of various pathological origin or the accompanying symptoms thereof.

According to the invention, the compounds of formulas (I) and (Ia) are prepared by a) reacting o-hydroxyacetophenone with an N-(p-substituted benzyl)-4-piperidone of formula (II),

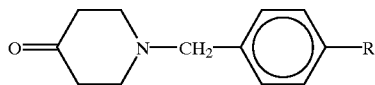

(II)

wherein R stands for halogen or nitro group or a straight or branched chain $C_{1-6}$ alkyl group in the presence of pyrollidine; or b) alkylating spiro[2H-1-benzopyran-2,4'-piperidine]-4(3H)-one of formula (IV) with a p-substituted benzyl halide of formula (III),

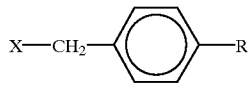

(III)

wherein R means halogen or nitro group or a straight or branched chain $C_{1-6}$ alkyl group and X means chlorine or bromine, in the presence of an acid binding agent, then if desired, converting a spiro[2H-1-benzopyran-2,4'-piperidine]-4(3H)-one derivative of formula (I), wherein R means a halogen or nitro group or a straight or branched chain $C_{1-6}$ alkyl group, obtained as a base, to its acid addition salt by treating it with an acid; and/or, if desired, liberating the base form of a spiro[2H-1-benzopyran-2,4'-piperidine]-4(3H)-one derivative of formula (I) wherein R means halogen or nitro group or a straight or branched chain $C_{1-6}$ alkyl group obtained as an acid addition salt, by treating it with a base; or c) quaternizing a spiro[2H-1-benzopyran-2,4'-piperidine]-4(3H)-one derivative of formula (IV)

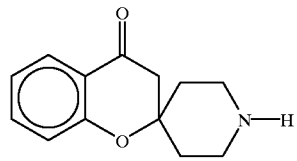

(IV)

4(3H)-one derivative of formula (I) or an acid addition salt thereof, wherein R means hydrogen, halogen, nitro group or a straight or branched chain $C_{1-6}$ alkyl group, with a benzyl halide of formula (III), wherein R means hydrogen, halogen or nitro group or a straight or branched chain $C_{1-6}$ alkyl group, and X represents chlorine or bromine, to obtain quaternary salts of formula (Ia), wherein R and R' are the same or different and are identical to said R but can mean also hydrogen; and $Z^-$ means one equivalent of an anion.

The hydrogen maleate salt of the known compound of formula (I) containing hydrogen as R is novel. The advantage of this salt over the free base form appears in the higher stability.

A common and definitive feature of cognition-enhancing, i.e. nootropic drugs occurs in their capability to enhance the resistance of learning and memory processes against influences inducing anterograde and retrograde amnesia. Impairment of learning and memory induced by various ways, e.g. by anticholinergic drugs (such as scopolamine), carbon dioxide poisoning, a high dose of an anxiolytic agent (such as diazepam) or electroshock are commonly accepted experimental animal models of memory and learning deficiencies developed in human disorders of various aetiology (such as Alzheimer's disease, parkinsonism, Huntington's chorea or vascular dementias and states after stroke accompanied by neurodegenerative injuries). It has been found that compounds of formulas (I) and (Ia) exert an excellent antiamnesic effect in these animal models and therefore, they are useful for the treatment of cognitive disturbances occurring in the diseases mentioned above.

The biological activity of the compounds of formulas (I) and (Ia) was studied by using passive avoidance test. This test is one of the most widely used animal experimental model for investigating the effects of substances on the cognitive functions (learning and memory processes). This is based on inhibition of the genetically determined behavior of rodents (mice and rats) that they prefer dark space to light one. A single electric shock given in the dark box is employed as a memory trace, the retention and retrieval of which can be controlled after a shorter or longer period.

1. Diazepam (DIA) Induced Anterograde Amnesia

The passive avoidance test was carried out on NMRI mice with a body weight of 25–28 g. During the learning, preselected animals (mice entering into a dark space from an illuminated space within 30 s) were placed into an illuminated space. After entering into the dark space, the animal received within 30 s onto his paw an electric shock (1 mA for 3 s) causing an unpleasant sensation. The time of entry into the dark space (latency period) was measured. During the check, after 24 hours, the animals were again put back to the illuminated space and the time elapsed until entry into the dark space (retention time) was measured (limit time= 300 s). The animals were intraperitoneally (i.p.) treated with 3 mg/kg of diazepam (chemically, 7-chloro-1,3-dihydro-1-methyl-5-phenyl-2H-1,4-benzodiazepin-2-one) 30 minutes before learning in order to induce anterograde amnesia. The compounds were orally (p.o.) administered in doses of 0.1 or 10 mg/kg, respectively one hour before the learning. The protective effect was calculated percentage value (P%) by using the following formula:

$$P\% = \frac{T_{treated+DIA} - T_{placebo+DIA}}{T_{placebo} - T_{placebo+DIA}} \times 100$$

2. Electoshock (ECS) Induced Retrograde Amnesia

In this test, the retrograde amnesia was induced on NMRI mice having a body weight of 24–26 g by using an auricular electroshock treatment of 20 mA for 0.2 s at one hour following the learning. The compounds to be tested were administered 2 hours after learning. The protective effect was calculated as percentage value (p%D) by using the following formula:

$$P\% = \frac{T_{placebo+ESC} - T_{placebo+ESC}}{T_{placebo} - T_{placebo+ESC}} \times 100$$

$P\% = T_{treated+ECS} - T_{placebo+ECS}/T_{placebo} - T_{placebo+ECS} \times 100$ In the above formula, T means the measured retention time of animals treated as shown in the index or the measured retention time of untreated animals, respectively. The results of experiments are summarized in the following Tables.

TABLE 1

Effect of spiro[2H-1-benzopyran-2,4'piperidine]-4(3H)-one derivatives on the diazepam induced anterograde amnesia

| Compound | Dose (mg/kg p.o.) | Prevention % |
|---|---|---|
| 4600592 | 0.1 | 144* |
|  | 10 | 92 |
| 4610351 | 0.1 | 78 |
|  | 10 | 176* |
| 4611109 | 0.1 | 92 |
|  | 10 | 0 |
| 4610282 | 0.1 | 131* |
|  | 10 | 24 |
| 4610350 | 0.1 | 170* |
|  | 10 | 29 |
| 4611265 | 0.1 | 86* |
|  | 10 | 134* |
| 4611266 | 0.1 | 159* |
|  | 10 | 105* |
| 4611267 | 0.1 | 47 |
|  | 10 | 67* |
| Vinpocetine | 0.1 | 0 |
|  | 10 | 123 |

* = p < 0.05 by the Mann-Whitney test in comparison to the diazepam control group.

TABLE 2

Effect of spiro[2H-1-benzopyran-2,4'-piperidine]4(3H)-one derivatives on the electroshock induced retrograde amnesia

| Compound | Dose (mg/kg) | Route of administration | Prevention % |
|---|---|---|---|
| TRH | 1 | i.p. | 77 |
|  | 10 | i.p. | 35 |
| 4600592 | 1 | p.o. | 48 |
|  | 10 | p.o. | 44 |
| 4610351 | 1 | p.o. | 81 |
|  | 10 | p.o. | 108* |
| 4610282 | 1 | p.o. | 77 |
|  | 10 | p.o. | 29 |
| 4610350 | 1 | p.o. | 0 |
|  | 10 | p.o. | 8 |

It can be seen from data of the Tables that the compounds of formulas (I) and (Ia) proved to be very effective in the diazepam-induced anterograde amnesia test of the so-called "one trial step-through passive avoidance" experiment, a method useful for measuring cognitive functions. The effects of compounds of the present invention were compared to those of drugs successfully employed in therapy. From the compounds, those of code numbers 4600592, 4610282, 4610351, 4610350, 4611265 and 4611266 significantly (in a percentage of 105–176 %) antagonized the amnesic effect of diazepam. Analogues containing bromine or nitro group as substituent (compounds 4611109 and 4610350) showed an antiamnesic action in lower doses (0.1 mg/kg) but were inactive in higher doses; while both lower doses (0.1 mg/kg) as well as higher doses (10 mg/kg) of the compounds of formulas (I) and (Ia) containing tertiary butyl group (compounds 4611266 and 4611265) provided nearly the same protection against the amnesic effect of diazepam.

Three substances exhibited antiamnesic effectivity in the ECS-induced retrograde amnesia test. The compound 4610351 could significantly reverse the ECS-caused amnesia in both doses: a significant value (108%) was obtained by the higher dose. A dose of 0.1 mg/kg of compound 4610282 provided 77% protection. No considerable protection was afforded in this test by the known compound 4600592 wherein R is hydrogen.

It can be seen that particularly compounds 4610282, 4610350, 4610351 and 4611266 from among the compounds of formula (I) as well as 4611265 from the derivatives of formula (Ia) possess a significant antiamnesic effect. Compound 4610351 has been investigated in detail both under in vitro and in vivo conditions. This compound evened 36% protection in an oral dose of 10 mg/kg in the normobaric hypoxia-induced memory deficiency model on rats; this surpassed the protective effect of 21% provided by 10 mg/kg oral dose of vinpocetine. The same compound significantly inhibited the $K^-$—or veratrine-induced uptake of $^{45}Ca^{++}$ by synaptosome preparation, a fact indicating the inhibitory action of the compound on the neuronal calcium uptake with the $IC_{50}$ values of 45.6 $\mu M$ ($K^+$-induced $^{45}Ca^{--}$ uptake) and 4.5 $\mu M$ (veratrine-induced $^{45}Ca^{--}$ uptake), respectively. On the basis of these investigations, compounds of formulas (I) and (Ia) can be utilized for the treatment of diseases and dementias accompanied by the impairment of cognitive processes (learning, memory), such as multiinfarct and Alzeimer type dementias, states following stroke, ischaemic injuries, sequels of trauma of the central nervous system, parkinsonism, Huntington's chorea or multiple sclerosis. The therapeutical doses of compounds of formulas (I) and (Ia) can range between 0.1 and 40 mg/kg of body weight given orally, daily once or several times.

Based on the statement of the prior art European patent application No. 0,431,943 A2 and J. Med. Chem. 35. 3973 (1992), according to which compounds of similar structure showed an antiarrhythmic action, our target compounds have also been tested from this viewpoint.

These experiments were carried out on rats (with a body weight of 180–200 g) anaesthetized by urethane (1.25 g/kg i.p.) in such a way that 50 $\mu g/kg$ of aconitine [chemically acetyl benzoyl aconine] was injected to the tail vein then, the arrhythmic disturbances were observed on ERG II lead after 5 minutes [J. Med. Exp. 10, 93 (1964)].

The compounds to be tested for antiarrhythmic effect were intravenously (i.v.) administered 2 minutes, or orally one hour before aconitine. (The route of administration is shown in the following Table.)

The aconitine arrhythmia was evaluated in such a manner that the severity of arrhythmia was characterized by an increasing number and, after average calculation both in the control as well as in the tested group, the average of treated group was expressed as percentage of the control. The arrhythmia was characterized by the following scores:

| Score | Symptoms |
| --- | --- |
| 0 | complete protection |
| 1 | sporadical ventricular extrasystoles |
| 2 | serial ventricular extrasystoles |
| 3 | bi- and trigeminy |
| 4 | ventricular tachycardia |
| 5 | ventricular fibrillation, death |

TABLE 3

Results of investigations on the antiarrhythmic effect

| Compound | Dose (mg/kg) | Route of administration | Inhibition (%) | $ED_{50}$ (mg/kg) |
| --- | --- | --- | --- | --- |
| Control | — | — | average score ≅ 3.9 | — |
| Bisaramil | 0.3 | i.v. | 20 | |
| | 0.5 | i.v. | 48 | 0.49 |
| | 1.0 | i.v. | 91 | |
| Quinidine | 0.3 | i.v. | 34 | |
| | 10.0 | i.v. | 55 | 6.66 |
| | 30.0 | i.v. | 83 | |
| Mexiletine | 1.0 | i.v. | 29 | |
| | 3.0 | i.v. | 68 | 2.51 |
| | 10.0 | i.v. | 62 | |
| Amiodarone | 3.0 | i.v. | 13 | |
| | 5.0 | i.v. | 29 | 7.04 |
| | 10.0 | i.v. | 70 | |
| 4600592 | 10 | i.v. | 3 | |
| | 30 | i.v. | 19 | — |
| | 30 | p.o. | 0 | |
| 4611265 | 10 | i.v. | 21 | |
| | 30 | i.v. | 10 | — |
| | 30 | p.o. | 0 | |
| 4611267 | 10 | i.v. | 0 | |
| | 30 | i.v. | 29 | — |
| | 30 | p.o. | 0 | |
| 4610351 | 10 | i.v. | 16 | |
| | 30 | i.v. | 16 | — |
| | 30 | p.o. | 5 | |
| 4611266 | 10 | i.v. | 21 | |
| | 30 | i.v. | 3 | — |
| | 30 | p.o. | 0 | |

Note: Code numbers shown in the Tables stand for the following compounds:
4600592: known compound of formula (I) where R is hydrogen
4610351: compound of formula (I) where R is chlorine
4611109: compound of formula (I) where R is bromine
4610282: compound of formula (I) where R is fluorine
4610350: compound of formula (I) where R is nitro
4611265: compound of formula (Ia) where R and R' are each nitro
4611266: compound of formula (I) where R is a tertiary butyl group
4611267: compound of formula (Ia) comprising R and R' are each hydrogen Amiodarone: (2-butyl-3-benzofuranyl)-{4-[2-diethylamino)ethoxy]-3,5-diiodophenyl}-ketone Bisaramil: 3-methyl-7-ethyl-9α-(4-chlorobenzoyloxy)-3,7-diazabicyclo[3.3.1]nonane hydrochloride Quinidine: (S)-(6-methoxy-4-quinolinyl)-[(2R.4S.5R)-5-vinyl-2-quinuclidinyl]methanol Mexiletine: 1-methyl-2-(2,6-xylyloxy)ethylamine TRH: 5-oxo-L-prolyl-L-histidyl-L-proline amide Vinpocetine: ethyl apovincaminate Evaluation of the Results When administered intravenously, aconitine elicites a well-reproducible arrhythmia concerning both the time (duration) and severity of effect. According to the evaluations (average score=3.9), the aconitine dose employed induced a very severe arrhythmia (ventricular tachycardia, fibrillation). Known antiarrhythmic agents inhibited the development of arrhythmia in a dose-dependent manner. The results obtained were in a good agreement with the previously published values [Orvostudomány 33, 347–361 (1982)]. The compounds according to the invention did not prevent the development of aconitine arrhythmia either through oral or intravenous application, i.e. the compounds of the invention did not exert any antiarrhythmic effect in the present model.

1-(4'-substituted benzyl)-4-piperidones (II), used as starting materials can be prepared by the reactions known from the literature:

a) Starting out of 4-substituted benzylamines the addition of this compound on two moles acrylic acid esters, the intramolecular ester condensation and the hydrolytic decarboxylation results in compound (II). [Helv. Chim. Acta, 41, 1188. (1958); J.Am. Chem.Soc., 68, 2108. (1946)].

b) Starting from 4-substituted benzylhalides the alkylating reaction of 4-piperidone monohydrate hydrochloride in the presence of acid binding agent yields the compound (II). [Synth. Comm., 20, 3537. (1990)].

The invention is illustrated in detail by the following non-limiting Examples.

EXAMPLE 1

Preparation of the Compounds of Formula (I) in Their Free Base Form by Spirocyclization a) A solution containing 0.22 mole of a 4-piperidone of formula (II) and 27.2 g (0.2 mole) of 2-hydroxyacetophenone in 100 ml of toluene was weighed into a round-bottom flask equipped with stirrer, reflux condenser and water separator device. After starting the stirring, 4 g (56 mmole) of pyrrolidine were dropped to the above mixture at room temperature. After addition, the reaction mixture was heated to the boiling point and the boiling was continued for additional 2–24 hours following the gradual separation of water. Then, the reaction mixture was cooled and poured into 150 ml of water. After separation of the phases, the aqueous layer was re-extracted with 50 ml of toluene. The combined toluene extra was washed with 10 ml of water and evaporated. The evaporation residue of the toluene phase was thoroughly mixed with diisopropyl ether until crystallization and, if desired, recrystallized from a protic polar solvent, e.g. ethanol to yield 60–75% of purified product.

b) 0,1 mmole of 4-piperidone of formula (II), 0,1 mole 2-hydro-acetophenone, 0.1 mole pyrrolidine are refluxed in methanol (25 ml) solution for 3–8 hours. The progress of the reaction is controlled by TLC. After cooling the reaction mixture the compound (1) crystallizes (if it does not occur during the heating period), which can be increased by cooling it in the refrigerator over night. Filtration and careful washing of the filtrate cake with cold methanol yields product (I) in 80–92% of the theoretical amount.

EXAMPLE 2

Preparation of the Compound of Formula (I) in Free Base Form by Alkylating the Acid Addition Salt of Spiro[2H-1-Benzopyran-2,4'-Piperidine]-4 (3H)-One A mixture of 25.4 g (0.1 mole) of spiro[2H-1-benzopyran-2,4'-piperidine-4(3H)-one hydrochloride was boiled under reflux with 0.105 mole of a compound of formula (III) and 17 g of sodium hydrogen carbonate in 50 ml of methanol. The boiling was continued until the starting spiro[2H-1-benzopyran-2,4'-piperidine]-4(3H)-one was consumed from the reaction mixture [as detected by thin layer chromatography (TLC)], which required 4–8 hours.

The compounds of formula (I) obtained could preferably be recovered from the reaction mixture as follows:

1) After filtering the hot reaction mixture, the filter cake was thoroughly washed once with 20 ml, then twice with 10 ml of water each. The methanolic mother liquor was not combined with the washings. The target compound of formula (I) was obtained in two generations: one as the solid phase washed on the filter and the other one as the substance precipitating from the methanolic mother liquor in crystalline form.

2) After evaporation of the methanolic mother liquor, the residue was thoroughly mixed with water. If the target compound of formula (I) precipitated in crystalline form, it was filtered; if precipitation did not occur, the aqueous mixture was extracted with an organic solvent (such as dichloromethane) and the extract was evaporated.

The target compound of formula (I) was recrystallized in each case. A $C_{1-3}$ alcohol (such as methanol, ethanol or isopropanol), an ether (e.g. diisopropyl ether), an ester (such as ethyl acetate) or acetonitrile could preferably be used for this purpose.

The same reagents can be used to carry out the alkylating reaction in other solvents as well; among them acetonitrile, and isopropanol have proved the most suitable. Usually the compound of formula (I) crystallizes out of these solvents and it can be separated contaminated by inorganic salts, by filtration. As compounds of formula (I) in form of free base are rather insoluble in water, the purification can be done easily. The cold organic solvents (methanol, isopropanol, acetonitrile) contain only a very limited quantity of compounds of formula (I), which can be isolated after the evaporation of the solvent and recrystallizing the remainder.

EXAMPLE 3

Preparation of Acid Addition Salts of the Compounds of Formula (I)

a) Preparation of Hydrochlorides

One mole of a compound of formula (I) as free base was stirred in 6 ml of hydrochloric acid solution of 0.5 mol/liter concentration at 50° C. for 15 minutes. After cooling (by keeping in a refrigerator for the higher yield) and filtering the solution, if desired, the precipitated hydrochloride was recrystallized from a protic solvent.

b) Preparation of Hydrochlorides

One mmole of a compound of formula (I) as free base is dissolved in organic solvent, i.e. in ethyl acetate (20 ml) or $C_{1-3}$ alcohol (10 ml) at boiling temperature. To the sharp solution of compound (I) free base a small excess of solution gaseous hydrogen chloride in the same solvent is added. The precipitate is increased by cooling the solution, and filtered. If it is desired the precipitate is crytallized out of organic solvents, mostly $C_{1-3}$ alcohol.

c) Preparation of Hydrogen Maleate Salts

One mmol of compound of formula (I) as free base was dissolved in an organic solvent (preferably ethanol or ether) and an ethereal solution containing 1.2 mmol of maleic acid was added. After filtering off, the precipitated hydrogen maleate salt was preferably recrystallized from ethanol.

The following compounds of formula (I) were prepared as described above:

| R | Salt/free base | Solvent of recrystallization | M.p. °C. |
|---|---|---|---|
| Cl | free base | methanol | 82–84 |
| Cl | hydrogen maleate | ethanol | 190–192 |
| Cl | hydrochloride | ethanol | 274–275 |
| H | free base | diisopropyl ether | 103–104* |
| H | hydrochloride | according a) | 275 (decomp.) |
| Br | free base | methanol | 93–95 |
| F | free base | ethanol | 117–119 |
| $NO_2$ | free base | ethanol | 133–135 |
| $(CH_3)_3C$- | free base | diisopropyl ether | 149–151 |
| $(CH_3)_3C$- | hydrochloride | according Example 3.b. | 282–285 (decomp.) |
| $(CH_3)_3C$- | hydrogen maleate | ethanol | 175–178 |
| $(CH_3)_3C$- | hydrogen fumarate | ethanol | 255–258 (decomp.) |

*The melting point of the known compound of formula (I) where R is hydrogen is 103–104° C. in opposition to 91–93° C. published in the literature. This compound could not be purified by using the method described in the literature since the desired product did not crystallize out of benzene or of a mixture of benzene and cyclohexane.

EXAMPLE 4

Simultaneous Preparation of Compounds of Formula (I) and Quaternary Salts of Formula (Ia) from Spiro[2H-1-Benzopyran-2,4'-Piperidine]-4(3H)-One of Formula (IV)

A mixture containing 2.54 g (0.01 mole) of spiro[2H-1-benzopyran-2,4'-piperidine]-4(3H)-one hydrochloride, 10 ml of methanol, 1.7 g of sodium hydrogen carbonate and 2.02 ml (0.011 mole) of 4- tertiary-butylbenzyl bromide was boiled under reflux for about 3 hours. In the course of boiling the solid phase was first dissolved, then a new solid phase precipitated. Subsequently, the reaction mixture was left to stand overnight in a refrigerator, then it was filtered in a cooled state. The obtained solid phase (3.10 g, which melted in a wide range) was mixed with 30 ml of toluene and again filtered. The obtained solid phase (1 g) was recrystallized from 25 ml of methanol to obtain 0.64 g of pure 1',1'-bis (4-tert-butylbenzyl)-spiro[2H-4(3H)-oxo-1-benzopyran-2,4'-piperidinium]bromide, m.p.: 255–258° C.

After evaporation of the toluene mother liquor and recrystallization of the evaporation residue (1.97 g) from 35 ml of diisopropyl ether, 1.5 g of pure 1'- (4-tert-butylbenzyl)-spiro [2H-1-benzopyran-2,4'-piperidine]-4(3H)-one were obtained, m.p.: 149–151° C.

EXAMPLE 5

Preparation of Quaternary Salts of Formula (Ia) from Spiro[2H-1-Benzopyran-2,4'-Piperidine]-4(3H)-One of Formula (IV)

A mixture coming 2.54 g (0.01 mole) of spiro[2H-1-benzopyran-2,4'-piperidine]-4(3H)-one hydrochloride, 5 ml of methanol, 1.7 g of sodium hydrogen carbonate and 2.53 ml (0.02 mole) of benzyl chloride was boiled under reflux for 3 hours, to yield 3.66 g of 1',1'-dibenzyl-spiro[2H-4(3H)-oxo-1-benzopyran-2,4'-piperidinium]hydrochloride which was recrystallize from methanol, m.p.: 262° C. (with decomposition).

EXAMPLE 6

Preparation of Quaternary Salts of Formula (Ia) From 1'-Benzyl-Spiro(2H-1-Benzopyran-2,4'-Piperidine]-4(3H)-Ones of Formula (I)

A mixture containing 3.07 g (0.10 mole) of 1'-benzyl-spiro[2H-1-benzopyran-2,4'-piperidine]-4(3H)-one, 15 ml of methanol and 1.3 g of benzyl chloride was boiled under reflux for 8 hours to result in 3.13 g of 1',1'-dibenzyl-spiro[2H-4(3H)-oxo-1-benzopyran-2,4'-piperidine] hydrochloride, which was identical to the product of Example 5. After recrystallization from methanol the product melted at 262° C. with decomposition.

EXAMPLE 7

Pharmaceutical Compositions a) Tablets of 100 mg weight containing 10 mg of active ingredient each

| Components: | g |
|---|---|
| Active ingredient | 50.0 |
| Lactose | 285.0 |
| Potato starch | 100.0 |
| Sodium dodecyl sulfate | 2.5 |
| Polyvinylpyrrolidone (Kollidon-K 90$^R$) | 5.0 |
| Microcrystalline cellulose (Avicel$^R$) | 50.0 |
| Vegetable oil (Sterotex$^R$) | 7.5 |

The above components were usually wet-granulated and then compressed to tablets of 100 mg weight containing 10 mg of active ingredient each.

b) Dragées of 125 mg weight containing 10 mg of active ingredient each

The tablets prepared as described above were coated in a known way by a coating consisting of sugar and talc. The dragées were polished with a mixture of bee wax and carnauba wax.

c) Capsules containing 20 mg of active ingredient each

| Components: | g |
|---|---|
| Active ingredient | 40.0 |
| Sodium lauryl sulfate | 12.0 |
| Lactose | 102.0 |
| Potato starch | 102.0 |
| Magnesium stearate | 2.4 |
| Colloidal silicon dioxide | 1.6 |

After thoroughly mixing the above components, the mixture obtained was filled into hard gelatine capsules containing 20 mg of active ingredient each.

What is claimed is:

1. A method of treating dementia in a mammalian subject which comprises the step of administering to a mammalian subject in need of said treatment, a therapeutically effective amount of a compound of the Formula (I)

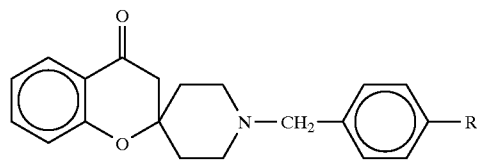

(I)

wherein

R is hydrogen, halogen, nitro, or a C1 to C6 straight or branched chain alkyl group, or a pharmaceutically acceptable acid addition salt thereof, or a quaternary salt of the Formula (Ia)

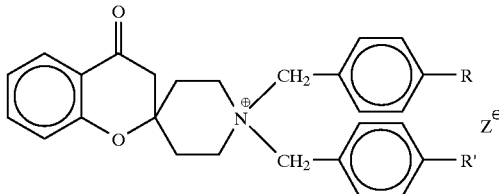

(Ia)

wherein

R and R' are each independently hydrogen, halogen, nitro, or a C1 to C6 straight or branched chain alkyl group, and Z− is one equivalent of an anion.

2. A compound of the Formula (I)

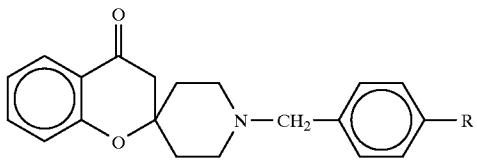

(I)

wherein R is halogen or t-butyl, or a pharmaceutically acceptable acid addition salt thereof, or a quaternary salt of the Formula (Ia)

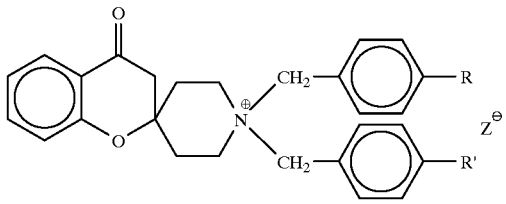

(Ia)

wherein R and R' are each independently hydrogen, halogen or t-butyl; and Z is one equivalent of an anion.

3. A compound of the Formula (I) as defined in claim 2 selected from the group consisting of 1'-(4-fluorobenzyl)-spiro{2H-1-benzopyran-2,4'-piperidine}-4(3H)-one;

1'-(4-chlorobenzyl)-spiro{2H-1-benzopyran-2,4'-piperidine}-4(3H)-one;

1'-(4-bromobenzyl)-spiro{2H-1-benzopyran-2,4'-piperidine}-4(3H)-one; and

1'-(4-tert-butylbenzyl)-spiro(2H-1-benzopyran-2,4'-piperidine)-4(3H)-one; or a pharmaceutically acceptable acid addition salt thereof; or a salt of the Formula (Ia) selected from the group consisting of 1',1'-bis(4-tert-butylbenzyl)-spiro{2H-4(3H)-oxo-1-benzopyran-2,4'-piperidinium}bromide and 1',1'-dibenzyl-spiro{2H-4(3H)-oxo-1-benzopyran-2,4'-piperidinium}chloride.

4. A pharmaceutical composition for the treatment of dementia which comprises a therapeutically effective amount of the compound of the Formula (I) as defined in claim 2, a pharmaceutically acceptable acid addition salt thereof, or a therapeutically effective amount of the quaternary ammonium salt of the Formula (Ia) as defined in claim 2; in combination with a pharmaceutically acceptable inert carrier.

5. The method of treating dementia in a mammalian subject defined in claim 1 wherein the compound of the Formula (I) is selected from the group consisting of 1'-(4-fluorobenzyl)-spiro{2H-1-benzopyran-2,4'-piperidine}-4(3H)-one;

1'-(4-chlorobenzyl)-spiro{2H-1-benzopyran-2,4'-piperidine}-4(3H)-one;

1'-(4-bromobenzyl)-spiro{2H-1-benzopyran-2,4'-piperidine}-4(3H)-one;

1'-(4-nitrobenzyl)-spiro{2H-1-benzopyran-2,4'-piperidine}-4(3H)-one; and

1'-(4-tert-butylbenzyl)-spiro{2H-1-benzopyran-2,4'-piperidine}-4(3H)-one; or a pharmaceutically acceptable acid addition salt thereof; or a salt of the Formula (Ia) selected from the group consisting of 1',1'-bis(4-tert-butylbenzyl)-spiro{2H-4(3H)-oxo-1-benzopyran-2,4'-piperidinium}bromide and 1',1'-dibenzyl-spiro{2H-4(3H)-oxo-1-benzopyran-2,4'-piperidinium}chloride.

6. A process for the preparation of a compound of the Formula (I)

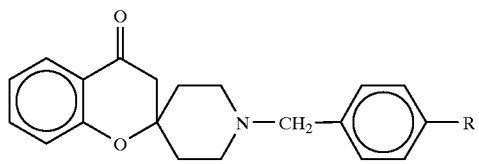

(I)

wherein

R is halogen or t-butyl, or a pharmaceutically acceptable acid addition salt thereof, or a quaternary salt of the Formula (Ia)

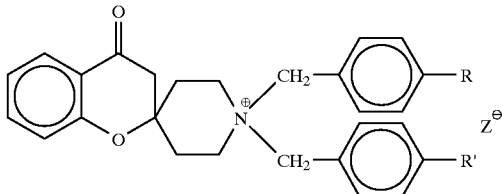

(Ia)

wherein

R and R' are each independently hydrogen, halogen, or t-butyl, and

Z− is one equivalent of an anion, which comprises alkylating a compound of the Formula (IV)

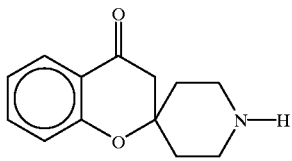

(IV)

or a pharmaceutically acceptable acid addition salt thereof with a compound of the Formula (III)

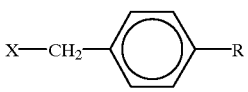

(III)

wherein

X is chlorine or bromine in the presence of an acid binding agent, or quaternizing a compound of the Formula (IV) or an acid addition salt thereof, or a compound of the Formula (I) or an acid addition salt thereof with a compound of the Formula (III) to obtain a quaternary salt of the Formula (Ia).

* * * * *